US006214352B1

(12) United States Patent
Matsukawa

(10) Patent No.: US 6,214,352 B1
(45) Date of Patent: Apr. 10, 2001

(54) TYROSINASE INHIBITING AGENT

(75) Inventor: Shinya Matsukawa, Tokyo (JP)

(73) Assignee: Matsukawa Kagaku Co., Ltd., Tokyo (JP)

( * ) Notice: Subject to any disclaimer, the term of this patent is extended or adjusted under 35 U.S.C. 154(b) by 0 days.

(21) Appl. No.: 09/478,333

(22) Filed: Jan. 6, 2000

(51) Int. Cl.[7] .......................... A01N 65/00; A61K 7/021; A61K 7/00; A61K 7/42
(52) U.S. Cl. .......................... 424/195.1; 424/59; 424/62; 424/401
(58) Field of Search .................................. 424/195.1, 59, 424/62, 401

(56) References Cited

FOREIGN PATENT DOCUMENTS

| | | |
|---|---|---|
| 60-104005 | 6/1960 | (JP) . |
| 50-135236 | 10/1975 | (JP) . |
| 64-26507 | 1/1989 | (JP) . |
| 3-157334 | 7/1991 | (JP) . |
| 3-193712 | 8/1991 | (JP) . |
| 5-139950 | 6/1993 | (JP) . |
| 6-65045 | 3/1994 | (JP) . |
| 6-128143 | 5/1994 | (JP) . |
| 6-336418 | 12/1994 | (JP) . |
| 7-25762 | 1/1995 | (JP) . |
| 7-61915 | 3/1995 | (JP) . |
| 8-99859 | 4/1996 | (JP) . |
| 10-182404 | 7/1998 | (JP) . |
| 10-265321 | 10/1998 | (JP) . |
| 10-265322 | 10/1998 | (JP) . |
| 10-279460 | 10/1998 | (JP) . |
| 10-279462 | 10/1998 | (JP) . |
| 10-330217 | 12/1998 | (JP) . |

OTHER PUBLICATIONS

Computer JPAB Abstract JP403193712 Watanabe et al Aug. 23, 1991.*
Computer DWPI Abstract JP 77044375 "Cosmetic for Whitening Human Skin . . . " Nov. 8, 1977.*
Computer JPAB Abstract JP406336418 Ryu et al, Dec. 6, 1994.*
Computer JPAB Abstract JP 03127714 Watanabe et al May 30, 1991.*

* cited by examiner

*Primary Examiner*—Herbert J. Lilling
(74) *Attorney, Agent, or Firm*—Griffin & Szipl, P.C.

(57) ABSTRACT

The tyrosinase inhibiting agent of this invention contains a solvent extract from at least one of Gardenia, Sophora and Rosa. When all three are present, it is preferred that the Gardenia extract be in the range of 15–30%, Sophora extract be in the range of 15–30%, and Rosa extract be in the range of 40–65%.

2 Claims, No Drawings

TYROSINASE INHIBITING AGENT

BACKGROUND OF THE INVENTION

1. Field of the Invention

The present invention relates to tyrosinase-inhibiting agents and further specifically relates to tyrosinase-inhibiting agents containing extracts or fractions prepared from Gardenia fruit, Sophora root, and Rosa fruit as the active ingredients. The tyrosinase-inhibiting agents of this invention may be used for improving the skin color and the like.

2. Description of the Related Art

Tyrosine, which is a type of amino acid, is converted by the action of tyrosinase enzyme into melanin, a black-brown to red-brown pigment, which is the cause of skin blemishes and spots. In order to prevent the production of melanin under the action of tyrosinase, various compounds have been used or proposed to inhibit the activity of tyrosinase in the fields of cosmetics and foods.

Representative examples of such compounds are ascorbic acid, sulfur compounds, hydroquinone, kojic acid, and natural plant extracts.

Ascorbic acid suffers from stability problems in the presence of moisture, while sulfur compounds have odor problems. Hydroquinone has a very high degree of efficacy, but has the shortcoming being highly toxic. Kojic acid and natural plant extracts have a high degree of safety but have weak tyrosinase-inhibiting activity, and in addition plant extracts often have odor and color problems.

In the recent years in view of the heightened interest by the society in cosmetics with a high degree of safety in promoting health, there is a need for tyrosinase-inhibiting agents which inhibit melanin production, which could be widely used in cosmetics, which are derived from natural products of high degree of safety, and which do not adversely affect the quality of the final product from the standpoint of taste or odor.

Japanese Patent Application Publications Showa 50-135236, Showa 60-104005, Showa 64-26507, Heisei 3-193712, Heisei 6-65045, Heisei 6-128143, Heisei 6-336418, Heisei 8-99859, Heisei 6-336418 and Heisei 8-99859 describe extracts of Gardenia, Sophora and Rosa which have tyrosinase-inhibiting activity.

Japanese Patent Application Publications Heisei 3-157334, Heisei 7-61915, Heisei 7-25762, and Heisei 5-139950 describe the uses of extracts of Gardenia, Rosa, or Sophora plants in the prevention and treatment of skin blemishes.

Japanese Patent Application Publications Heisei 10-279462, Heisei 10-279460, Heisei 10-265322, Heisei 10-265321, Heisei 10-182404, Heisei 10-330217 describe the use of Rosa or Sophora plant extracts as tyrosinase-inhibiting agents.

However, none of these show effective efficacy as a tyrosinase-inhibiting agent.

SUMMARY OF INVENTION

The present invention is aimed at proposing a novel tyrosinase-inhibiting agent which satisfies the need.

In order to achieve this objective, the present invention proposes a tyrosinase-inhibiting agent containing as the active ingredients three types of extracts obtained by extracting the Gardenia jasminoides fruit, Sophora flavescens root and Rosa multiflora fruit with an aqueous or hydrophilic solvent or a mixture thereof.

For example, if the tyrosinase-inhibiting agent is to be composed entirely of these three extracts, it is preferable that the Gardenia extract be present in the range of 15–30%, Sophora extract in the range of 15–20%, and Rosa extract in the range of 40–70%.

The present invention further proposes cosmetics which contain the three types of extracts made from the Gardenia, Sophora and Rosa.

The cosmetics contain, for example, Gardenia extract in the range of 15–30%, Sophora extract in the range of 15–30%, and Rosa extract in the range of 40–70%.

Through the use of the present invention, it is possible to propose a tyrosinase-inhibiting agent which can be widely used in cosmetics, which is made of highly safe natural products, and which do not adversely affect the quality of the final product from the standpoint of taste or odor.

The above and other objectives and advantageous features of the present invention will be made apparent from the description made with reference to the accompanying drawings, in which like reference characters designate the same or similar parts throughout the drawings.

DESCRIPTION OF THE PREFERRED EMBODIMENTS

Preferred embodiments in accordance with the present invention will be explained herein below with reference to drawings.

Gardenia jasminoides is a plant in the Rubiaceae family, and its fruit has been used as Kampo medicinal herb as an antipyretic, anti-inflammatory and hemostatic drug.

Sophora flavescens is a plant in the Leguminosae family and has been used as astringent/cathartic drug. It has also been used in cosmetics as an anti-microbial agent.

Rosa multiflora is the multiflora rose of the Rosaceae family, the mature fruit of which when dried has been used as a cathartic agent and diuretic. In cosmetics, it has been used as an antimicrobial agent.

The Gardenia fruit, Sophora root and Rosa fruit are ground in an appropriate manner and extracted using as the solvent of water, hydrophilic organic solvent or a mixture thereof. Organic solvents used for extraction are most appropriately especially, lower alcohols such as methanol and ethanol, and polyvalent alcohols such as 1,3-butylene glycol. The method of extraction is not particularly restricted, and the active ingredients can be extracted by immersing in the solvent maintained at room temperature to a temperature near the boiling point.

The tyrosinase-inhibiting agent of this invention when used as a mixture of 15–30% as Gardenia extract, 15–30% Sophora extract and 40–65% Rosa extract has an efficacy that is better than the product containing a single component.

When the tyrosinase-inhibiting agent of the present invention is used in cosmetics, it may be used in combination with other appropriate agents such as physiologically active agents which are generally used as components of cosmetics, for example astringents, antimicrobial agents and disinfectants, whitening agents, ultraviolet light absorbing agents, moisturizing agents, cell activating agents, anti-inflammatory and anti-allergy agents, anti-oxidant and activated oxygen removing agents. In such cases, synergistic effects with other effective ingredients may give effects which are superior to the normally expected degree of efficacy.

Specific examples of cosmetic components which can be used with the tyrosinase-inhibiting agents of this invention are as follows.

Astringents: citric acid or its salts, tartaric acid or its salts, aluminum chloride, aluminum sulfate, potassium sulfate, Ficus extract, Hamamelis extract, Geranium extract, Artemisia extract, Salvia extract, Aesculus extract, Equisetum extract, Melissa extract, and the like.

Antimicrobials and disinfectants: benzoic acid, sodium benzoate, benzetonium chloride, salicylic acid, sodium salicylate, sorbic acid, resorcin, bisabolol, hinokitiol, menthol, chitosan, Kalimeris extract, Eriobotrya extract, Yucca extract, Aloe extract, and the like.

Whitening agents: Ascorbic acid and its derivatives, sulfur, kojic acid and its derivatives, glucosamine and its derivatives, glutathione, Arnica extract, Scutellaria root extract, Morus extract, Bupleurum extract, Coix extract, Aesculus extract, oil-soluble Glycyrrhizae extract (Glycyrrhizae hydrophobic flavones, glabridin, glabrene, licochalcone A) and the like.

Ultraviolet absorbing agents: beta-isopropyl furanone derivatives, urocanic acid, oxybenzone, para-aminobenzoic acid, octyl methoxycinnamate, titanium oxide, beta-carotene, gamma-oryzanol, Aloe extract, rice bran extract, Chamomile extract, Crataegus extract, and the like.

Moisturizing agents: serine, glycine, alanine, collagen, hydrogenated collagen, keratin, elastin, royal jelly, chondroitin heparin, pectin, bifidobacterium fermentation products, Lactobacillus fermentation products, yeast extract, jojoba oil, Coix extract, Rehmannia extract, Zizyphus extract, Aloe arborescens extract, burdock extract, and the like.

Cell stimulating agents: Riboflavin and its derivatives, pyridoxine and its derivatives, nicotinic acid and its derivatives, pantothenic acid and its derivatives, alpha-tocopherol and its derivatives, carrot extract, Acanthopanax extract, Luffa extract, Tibouchina extract, Betula extract, Paeonia extract, Sapindus extract, Carthamus extract, garlic extract, and the like.

Anti-inflammatory and anti-allergy agents: Azulene, allantoin, aminocaproic acid, indomethacin, lysozyme hydrochloride, glycyrrhizic acid and its derivatives, glycyrrhetinic acid and its derivatives, tranexamic acid and its derivatives, Perilla extract, Coptis extract, Achiella extract, Tilia extract, Artemisia extract, Gentasiana extract, and the like.

Antioxidants and activated oxygen removing agents: Dibutyl hydroxytoluene, propyl gallate, baicalin, baicalein, superoxide dismutase, catalase, rosemary extract, Eriobotrya extract, sage extract, eucalyptus extract, royal extract, turmeric extract, nutmeg extract, hop extract and the like.

Cosmetics containing whitening agents may be manufactured in the form of emulsion, lotion, cream, jelly, and pack type cosmetics by standard methods using general components used in the manufacture of cosmetics, such as the oil components, detergents, moisturizing agents, fragrances, water, alcohol, thickening agents, colors, etc., and the tyrosinase-inhibiting agent of this invention can be added at any appropriate step in the manufacturing process.

The tyrosinase-inhibiting agent of this invention essentially does not interfere with the selection of the other components present in the cosmetics. In addition the following generally used cosmetic components can also be added.

Oil components: soy bean oil, flax seed oil, Paulownia oil, sesame oil, safflower oil, corn oil, almond oil, coconut oil, castor oil, rapeseed oil, olive oil, and the like.

Wax components: Carnauba wax, beeswax, spermaceti wax, cerax[1], lanolin, and the like.

[1]Phonetic translation

Hydrocarbons: liquefied paraffin, Vaseline, secilene[2], squalane, and the like.

[2]Phonetic translation

Fatty lipids: stearic acid, linoleic acid, oleic acid, lanolin, myristic acid, palmitic acid, hebenic acid[3], undecylenic acid, and the like.

[3]Phonetic translation

Alcohols: lauryl alcohol, cetyl alcohol, stearyl alcohol, oleyl alcohol, glycerin, propyl alcohol, 1,3-butylene glycol, ethylene glycol, cholesterol, phytosterol, and the like.

Esters: Decyl oleate, myristyl myristate, propylene glycol monostearate, lanolin acetate, trimyristate glycerin, propylene glycol dioleate, and the like.

Surface active agents: Anionic detergents, cationic detergents, zwitterionic detergents, etc.

Fragrances: menthol, carvone, eugenol, annetol, mint oil, spearmint oil, peppermint oil, eucalyptus oil, anise oil, etc.

The present invention is described in further detail using the examples below. The $IC_{50}$ used to describe the tyrosinase-inhibitory activity in Example 1 is such that the smaller numbers indicate stronger tyrosinase-inhibitory activity.

EXAMPLE 1

(Method for measurement of tyrosinase-inhibitory activity)

A mixture of 0.5 ml 0.5% tyrosine solution, 0.7 ml tyrosinase solution (60 μg/ml), and 1.8 ml of 1/15M phosphate buffer (pH 6.8), to which tyrosinase inhibitory agent has been added, is well mixed, and after reacting at 37° C. for 1 hour, absorption A is measured at 475 nm. Absorbance A is proportional to the concentration of colored components such as melanin produced by the tyrosinase. Absorbance B at 485 nm with no tyrosinase inhibitory agent added is also measured, and the tyrosinase inhibition rate is calculated as follows:

Inhibition rate (%)=(1−A/B)×100

Sample concentrations are varied in steps, and the inhibition rate is calculated. $IC_{50}$ is the sample concentration at which the inhibition rate calculated by interpolation is 50%.

| Sample | $IC_{50}$ (μg/ml) |
| --- | --- |
| Gardenia water extract | 310 |
| Gardenia ethanol extract | 400 |
| Gardenia water/ethanol (1:1) extract | 330 |
| Sophora water extract | 415 |
| Sophora ethanol extract | 320 |
| Sophora water/ethanol (1:1) extract | 350 |
| Rosa water extract | 115 |
| Rosa ethanol extract | 95 |
| Rosa water/ethanol (1:1) extract | 100 |
| Gardenia, Sophora, Rosa (1:1:1) | 155 |
| Gardenia, Sophora, Rosa (1:1:2) | 85 |
| Gardenia, Sophora, Rosa (1:1:4) | 75 |
| Gardenia, Sophora, Rosa (1:1:5) | 135 |

EXAMPLE 2

A neutral cream with whitening activity was prepared by homogenizing the components below using a conventional cream manufacturing method.

| | |
|---|---|
| stearic acid | 2 parts |
| stearyl alcohol | 7 parts |
| reduced lanolin | 2 parts |
| squalane | 5 parts |
| octyl dodecanol | 6 parts |
| polyoxyethylene cetyl ether | 3 parts |
| glycerin monostearate | 2 parts |
| fragrance | 0.1 parts |
| antimicrobials, antioxidants | 0.1 parts |
| propylene glycol | 5 parts |
| Gardenia extract | 1.5 parts |
| Sophora extract | 1.5 parts |
| Rosa extract | 4 parts |

Purified water added to give 100 parts.

EXAMPLE 3

An emulsion with whitening activity was prepared by emulsifying the components below using a conventional emulsion manufacturing method.

| | |
|---|---|
| stearic acid | 2 parts |
| Cetanol | 1.5 parts |
| Vaseline | 3 parts |
| lanolin alcohol | 2 parts |
| liquefied paraffin | 10 parts |
| polyoxyethylene monooleate ester | 2 parts |
| fragrance | 0.1 parts |
| antimicrobials, antioxidants | 0.1 parts |
| glycerin | 3 parts |
| propylene glycol | 5 parts |
| triethanolamine | 1 part |
| Gardenia extract | 2 parts |
| Sophora extract | 2 parts |
| Rosa extract | 5 parts |

Purified water added to give 100 parts.

While the present invention has been described in connection with certain preferred embodiments, it is to be understood that the subject matter encompassed by way of the present invention is not to be limited to those specific embodiments. On the contrary it is intended for the subject matter of the invention to include all alternatives, modifications and equivalents as can be included within the spirit and scope of the following claims.

The entire disclosure of Japanese Patent Application No. 10-16841 filed on Jun. 16, 1998 including specification, claims, drawings and summary is incorporated herein by reference in its entirety.

What is claimed is:

1. Tyrosine-inhibiting agent comprising extracts of Gardenia fruit in the range of 15–30%, extracts of Sophora root in the range of 15–30%, and extracts of Rosa fruit in the range of 40–70%; whereby the extracts of said Gardenia fruit, Sophora root and Rosa fruit are obtained by extracting with a solvent selected from the group consisting of water, hydrophilic organic solvent and mixtures thereof.

2. Cosmetic comprising extracts of Gardenia fruit in the range of 15–30%, extracts of Sophora root in the range of 15–30%, and extracts of Rosa fruit in the range of 40–70%; whereby the extracts of said Gardenia fruit, Sophora root and Rosa fruit are obtained by extracting with a solvent selected from the group consisting of water, hydrophilic organic solvent and mixtures thereof.

* * * * *